US010769363B2

(12) United States Patent
Leitner

(10) Patent No.: US 10,769,363 B2
(45) Date of Patent: Sep. 8, 2020

(54) SYSTEM AND METHODS FOR TRANSMITTING CLINICAL DATA HAVING MULTI-SEGMENT FIELDS FROM ONE OR MORE MODALITIES TO A DICTATION MACHINE

(71) Applicant: HYLAND SWITZERLAND SARL, Geneva (CH)

(72) Inventor: Christopher Eugene Leitner, Peoria, AZ (US)

(73) Assignee: HYLAND SWITZERLAND SÀRL, Geneva (CH)

( * ) Notice: Subject to any disclaimer, the term of this patent is extended or adjusted under 35 U.S.C. 154(b) by 979 days.

(21) Appl. No.: 15/160,851

(22) Filed: May 20, 2016

(65) Prior Publication Data

US 2017/0132397 A1 May 11, 2017

Related U.S. Application Data

(63) Continuation-in-part of application No. 14/984,795, filed on Dec. 30, 2015.
(Continued)

(51) Int. Cl.
*G06F 40/186* (2020.01)
*G16H 10/40* (2018.01)

(52) U.S. Cl.
CPC .......... *G06F 40/186* (2020.01); *G16H 10/40* (2018.01)

(58) Field of Classification Search
CPC ...... G06F 17/248; G06F 19/00; G06F 40/186; G16H 10/40
See application file for complete search history.

(56) References Cited

U.S. PATENT DOCUMENTS 9,092,964 B1 * 7/2015 Chan ................... G08B 21/02
9,235,605 B2 * 1/2016 Westin ................ G06F 17/3028
(Continued)

FOREIGN PATENT DOCUMENTS

WO 2011047200 A2 4/2011

OTHER PUBLICATIONS

Leitner, C., U.S. Appl. No. 14/984,795, filed Dec. 30, 2015.
(Continued)

*Primary Examiner* — Mark D Featherstone
*Assistant Examiner* — Faezeh Forouharnejad
(74) *Attorney, Agent, or Firm* — Medley, Behrens & Lewis, LLC

(57) ABSTRACT

A method of retrieving data from a Health Level 7 (HL7) clinical data from one or more modalities for transferring to a dictation system is disclosed. The method includes receiving HL7 clinical data having one or more multi-segment fields from a modality that generates the HL7 clinical data; accessing a formatting template for use in normalizing the parsed HL7 clinical data, the formatting template including a retrieval setting that specifies a type of the one or more multi-segment fields from which to retrieve the one or more values; retrieving the values from the fields of the one or more multi-segment fields based on the retrieval setting as specified in the formatting template; normalizing the retrieved values using format settings set in the formatting template; and sending the normalized values to the dictation system for use in generating a report by the dictation system.

19 Claims, 15 Drawing Sheets

Related U.S. Application Data

(60) Provisional application No. 62/253,656, filed on Nov. 10, 2015.

(56) References Cited

U.S. PATENT DOCUMENTS

| | | | |
|---|---|---|---|
| 9,268,761 B2* | 2/2016 | Baldwin | G06F 17/248 |
| 9,996,670 B2* | 6/2018 | Dejori | G16H 50/70 |
| 10,055,492 B2 | 8/2018 | Leitner et al. | |
| 2002/0194502 A1* | 12/2002 | Sheth | G06F 17/30873 |
| | | | 726/4 |
| 2003/0014557 A1 | 1/2003 | Berger et al. | |
| 2005/0075544 A1 | 4/2005 | Shapiro et al. | |
| 2006/0265508 A1 | 11/2006 | Angel et al. | |
| 2008/0021709 A1* | 1/2008 | Greer | G06F 19/00 |
| | | | 704/258 |
| 2010/0138239 A1* | 6/2010 | Reicher | G06F 17/243 |
| | | | 705/3 |
| 2012/0221346 A1* | 8/2012 | Acker | G06Q 10/00 |
| | | | 705/2 |
| 2013/0179183 A1* | 7/2013 | Wagner | G06Q 10/0637 |
| | | | 705/2 |
| 2013/0325505 A1 | 12/2013 | Vengco | |
| 2016/0019365 A1 | 1/2016 | Ober, Jr. | |
| 2017/0097740 A1* | 4/2017 | Kimber | H04L 67/02 |
| 2017/0132320 A1 | 5/2017 | Leitner | |
| 2017/0132321 A1 | 5/2017 | Leitner | |
| 2017/0132375 A1 | 5/2017 | Leitner | |

OTHER PUBLICATIONS

Leitner, C., U.S. Appl. No. 15/160,952, filed May 20, 2016.
Leitner, C., U.S. Appl. No. 15/393,655, filed Dec. 29, 2016.
Notice of Allowance from U.S. Appl. No. 15/160,952, dated Apr. 20, 2018.
Non-Final Office Action from U.S. Appl. No. 14/984,795, dated Oct. 2, 2018.
Forouharnejad, Faezeh, "Final Office Action for U.S. Appl. No. 14/984,795", dated Jul. 10, 2019, 39 pages.

\* cited by examiner

600

610
MSH | ^~\& | PACSGEAR HL7 | 636 | PACSGEAR
HL7 | PACSGEAR | 20140506135035 | ORU^R01 | 6353498103541253590 | P | 2.3 | | | |
USA | | |
| | | | | | | |
PID | | 000-00-
9988^^ | 297001^0^M10 | | ZZICCPRS^PATIENT^MTEST | | 19401010 | M | | | | | | | | | | |
0000099
88 | | | | | | | | | | | |
OBR | | | 6899878.8966-1^012110-3037^L | 70250^X-RAY EXAM OF SKULL^C4^1006^HEAD
MRI SCREENING^99RAP | | | 201001211033-0600 | " " | " " | | | | | 201001211215-
0600 | | 19341^TEST^TEST^L | | | IC/EMERGENCY DEPT MD DAY | | 57^IC/OUTSIDE
IMAGES^816^ CITY VAMC | | 201001211233-
0600 | | | F | | | | | | | 30873^SUN^TEST | | 30873^SUN^TEST | 201001211033
-0600 | | | | | | | | | | |

Segment 605

620     615

605 {
OBX | | CE | P^PROCEDURE^L | | 1006^HEAD MRI SCREENING^L | | | | | | C | | | | | | | | | | | |
OBX | | TX | I^IMPRESSION^L | | Normal study.   | | | | | | C | | | | | | | | | | |
OBX | | TX | R^REPORT^L | | Procedure: 2 views of the skull.   | | | | | | C | | | | | | | | | | |
OBX | | TX | R^REPORT^L | |    | | | | | | C | | | | | | | | | | |
OBX | | TX | R^REPORT^L | | Normal study.   | | | | | | C | | | | | | | | | | |
OBX | | TX | R^REPORT^L | |    | | | | | | C | | | | | | | | | | |
OBX | | TX | R^REPORT^L | |    | | | | | | C | | | | | | | | | | |
OBX | | TX | R^REPORT^L | | Addendum: Addendum: Normal procedure.
   | | | | | | C | | | | | | | | | | |
OBX | | TX | M^MODIFIERS^L | | STAT | | | | | | C | | | | | | | | | | |

SYSTEM AND METHODS FOR TRANSMITTING CLINICAL DATA HAVING MULTI-SEGMENT FIELDS FROM ONE OR MORE MODALITIES TO A DICTATION MACHINE

CROSS REFERENCES TO RELATED APPLICATIONS

Pursuant to 37 C.F.R. § 1.78, this application is a continuation-in-part application and claims the benefit of the earlier filing date of application Ser. No. 14/984,795 (now published as U.S. 2007/0132320 filed Dec. 30, 2015 entitled "System and Methods for Transmitting Health Level 7 Data from One or More Modalities to a Dictation System," which itself is related and claims priority under 35 U.S.C. § 119(e) to U.S. provisional patent application No. 62/253,656, filed Nov. 10, 2015, entitled, "System and Methods for Transmitting Health Level7 Data from One or More Modalities to a Dictation System." The content of each of the above applications is hereby incorporated by reference as if fully set forth herein. The present application is related to U.S. patent application Ser. No. 15/166,952 (now patented as U.S. Pat. No. 10,055,492), entitled "System and Methods for Transmitting Clinical Data from One or More Sending Applications to a Dictation System," filed contemporaneously herewith, and U.S. patent application Ser. No. 15/393,655 (now published as U.S. 2017/0132375), entitled, "System and Methods for Transmitting Clinical Data from One or More Sending Applications to a Dictation System," filed Dec. 29, 2016.

STATEMENT REGARDING FEDERALLY SPONSORED RESEARCH OR DEVELOPMENT

None.

REFERENCE TO SEQUENTIAL LISTING, ETC.

None.

BACKGROUND

1. Technical Field

The present invention relates generally to a system and methods of transferring clinical data from one or more sending applications to one or more dictation systems. Specifically, it relates to a system and methods of transferring clinical data generated from one or more sending applications associated with the one or more data sources to at least one dictation system for use in generating reports at the at least one dictation system.

2. Description of the Related Art

In a typical hospital environment, a medical technician or a radiologist performs tests on a patient to measure some vital statistics using a modality or modality equipment such as, for example, an ultrasound machine. When the radiologist performs the test, the modality generates results that may be in a standard structured data such as, for example, DICOM Structured Report (SR) or Health Level-7 (HL7) messages. The results are then memorialized on paper, either manually by the medical technician or printed on the paper using an imaging device communicatively connected with the modality. To transfer the numerical data generated by the modality, the radiologist may read or dictate the results on the paper into a dictation system. The dictation system then receives the results, transcribes the numerical data and generates reports using the transcribed data.

Dictation is not an optimal workflow solution for reporting numerical results to a reporting tool. Transcription errors may occur when dictating measurements from handwritten paper forms. Further, recording the measurements from the modality, printing them and then having a user dictate the printed measurements into a dictation system to generate reports may be time consuming and require human resources. One existing solution to help more efficiently process DICOM content and reduce risks of errors involves an application that receives DICOM messages, normalizes the DICOM content and prepares it for use in generating reports using dictation systems.

However, modalities that generate HL7 content still require the manual process of printing the HL7 content and having the HL7 results dictated into a dictation system by a user. Moreover, HL7 content may contain multiple segments that require certain pre-processing in order to select the desired data to be formatted and forwarded to a dictation system.

Accordingly, there is a need for a system and methods of more efficiently selecting HL7 specific data and transferring the selected HL7 data to a dictation system in a format compatible with report templates contained in the dictation system and without the potential errors that may occur when dictating displayed, handwritten or printed modality results into the dictation system.

SUMMARY

A system and methods of transferring data generated by one or more modalities to one or more dictation systems are disclosed. A method of transferring HL7 content from one or more modalities to a dictation system for use in generating reports includes receiving Health Level 7 (HL7) clinical data from at least one modality that generates HL7 clinical data. The method also includes parsing the HL7 clinical data received from at least one modality to retrieve one or more values from the HL7 clinical data that match one or more fields in a template. The method may include accessing a formatting section in the template for use in normalizing the parsed HL7 clinical data, the formatting section including one or more fields from a specified type of the one or more multi-segment fields to be retrieved; retrieving one or more values from the one or more fields from each of the specified type of the one or more multi-segment fields from the parsed HL7 clinical data; and normalizing the retrieved one or more values from the one or more fields from each of the specified type of multi-segment fields by formatting the retrieved one or more values using one or more format settings set in the formatting section of the template; and The one or more normalized values may be mapped to at least one field in a report template in the dictation system by associating the one or more normalized values to the at least one field in the report template for use in generating a report by the dictation system. The one or more normalized values may then be sent to the dictation system, wherein the dictation system generates the report containing the one or more normalized values.

From the foregoing disclosure and the following detailed description of various example embodiments, it will be apparent to those skilled in the art that the present disclosure provides a significant advance in the art of normalizing and transferring HL7 content generated by one or more modalities to one or more dictation systems. Additional features and advantages of various example embodiments will be better understood in view of the detailed description provided below.

BRIEF DESCRIPTION OF THE DRAWINGS

The above-mentioned and other features and advantages of the present disclosure, and the manner of attaining them, will become more apparent and will be better understood by reference to the following description of example embodiments taken in conjunction with the accompanying drawings. Like reference numerals are used to indicate the same element throughout the specification.

FIG. 6 shows an example HL7 message with multi-segment fields.

FIG. 8 shows user interface displaying an example OBX segment with a field selected by the user.

FIG. 9A shows an example user interface for selecting a field from which values will be extracted from repeating segments and concatenated.

FIG. 9B shows an example user interface where a user may select multiple fields from which values will be extracted from the repeating segments and concatenated together.

FIG. 10 shows an example user interface of application for creating an ID/value pair from the repeating segment.

FIG. 11 shows an example user interface showing configurable options for use in setting an if/then statement.

DETAILED DESCRIPTION OF THE DRAWINGS

Figure 1:
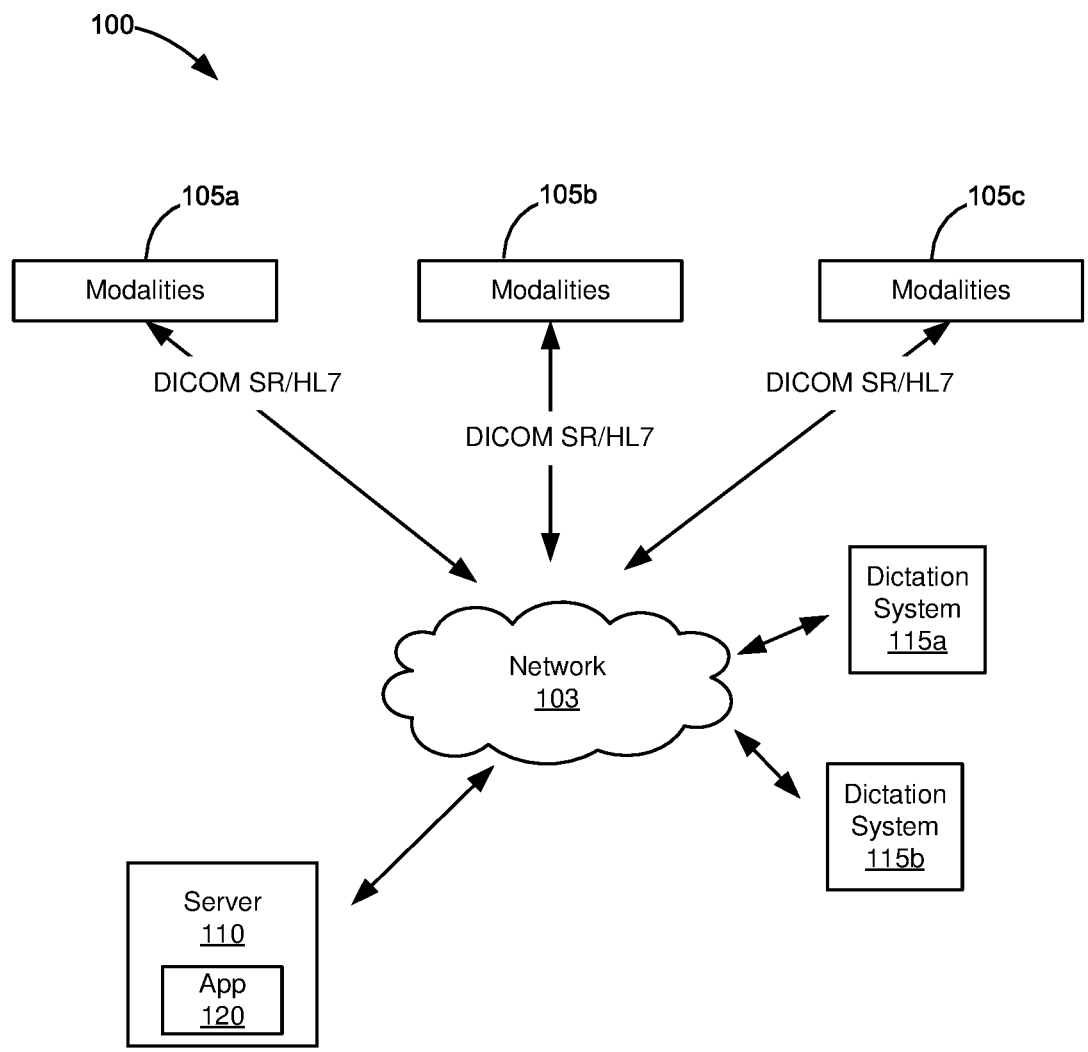
FIG. 1 shows one example block diagram of a modalities to dictation transfer system.

It is to be understood that the disclosure is not limited to the details of construction and the arrangement of components set forth in the following description or illustrated in the drawings. The disclosure is capable of other example embodiments and of being practiced or of being carried out in various ways. For example, other example embodiments may incorporate structural, chronological, process, and/or other changes. Examples merely typify possible variations. Individual components and functions are optional unless explicitly required, and the sequence of operations may vary. Portions and features of some example embodiments may be included in or substituted for those of others. The scope of the disclosure encompasses the appended claims and all available equivalents. The following description is, therefore, not to be taken in a limited sense, and the scope of the present disclosure is defined by the appended claims.

Also, it is to be understood that the phraseology and terminology used herein is for the purpose of description and should not be regarded as limiting. The use herein of "including," "comprising," or "having" and variations thereof is meant to encompass the items listed thereafter and equivalents thereof as well as additional items. Further, the use of the terms "a" and "an" herein do not denote a limitation of quantity but rather denote the presence of at least one of the referenced item.

In addition, it should be understood that example embodiments of the disclosure include both hardware and electronic components or modules that, for purposes of discussion, may be illustrated and described as if the majority of the components were implemented solely in hardware.

It will be further understood that each block of the diagrams, and combinations of blocks in the diagrams, respectively, may be implemented by computer program instructions. These computer program instructions may be loaded onto a general purpose computer, special purpose computer, or other programmable data processing apparatus to produce a machine, such that the instructions which execute on the computer or other programmable data processing apparatus may create means for implementing the functionality of each block or combinations of blocks in the diagrams discussed in detail in the description below.

These computer program instructions may also be stored in a non-transitory computer-readable medium that may direct a computer or other programmable data processing apparatus to function in a particular manner, such that the instructions stored in the computer-readable medium may produce an article of manufacture, including an instruction means that implements the function specified in the block or blocks. The computer program instructions may also be loaded onto a computer or other programmable data processing apparatus to cause a series of operational steps to be performed on the computer or other programmable apparatus to produce a computer implemented process such that the instructions that execute on the computer or other programmable apparatus implement the functions specified in the block or blocks.

Accordingly, blocks of the diagrams support combinations of means for performing the specified functions, combinations of steps for performing the specified functions and program instruction means for performing the specified functions. It will also be understood that each block of the diagrams, and combinations of blocks in the diagrams, can be implemented by special purpose hardware-based computer systems that perform the specified functions or steps, or combinations of special purpose hardware and computer instructions.

Disclosed are an example system and example methods for receiving results generated by one or more modalities in one or more formats or standards to which the modalities adhere. One example method may include one or more instructions stored in a non-transitory computer readable storage medium that transfers structured report measurements from one or more modalities directly into a dictation system such as, for example, a medical dictation system. In an alternative example embodiment, the structured report measurements may be transferred to the dictation system through a sending application associated with the source modality with which the measurements were captured. Using DICOM Structured Report (SR) or HL7 measurement data from modalities that generate these data respectively (e.g. DEXA, ultrasound and CT), the example method auto-populates a report template in the dictation system to generate a report, saving valuable radiologist dictation time and reducing potential human error. One example method includes one or more instructions that deliver data directly to dictation systems. The disclosed example system and example methods also include tools for quick configuration and normalization of incoming measurements. Normalization may be performed using protocol-specific formatting templates that may be set up by a user in an application that receives the incoming measurement data from a specific modality.

One example method may automatically populate clinical worksheets and forms in one or more dictation systems with values from modalities, saving manual dictation time. One example method may be accessible through a user interface in an application, may receive messages containing measurements from modalities on specific ports, and may place those messages into meaningful matching groups. Formatting templates that normalize the messages may be assigned to matching groups such that all incoming messages from modalities that belong in a matching group may be normalized using the assigned formatting templates. Values in matching groups may be mapped to report template fields that correspond to fields in a report that will be generated by a dictation system using the values from the modalities. After the mapping and normalization, the mapped data may then be forwarded to the dictation system where the mapped and formatted values are auto-populated to the corresponding fields in the report template at the dictation system to generate a report.

In one example embodiment, the modalities may generate HL7 messages. The method includes parsing the HL7 messages to identify the relevant data, normalizing the data to follow a format set or defined by a user-configurable formatting template, and sending the normalized data to a dictation system. The present example system and example methods aim to improve the numerical dictation process by automating the transfer of data from the modalities to the reporting and/or dictation systems, offering the potential to eliminate paper scanning and manual transcription of numerical results from the modalities to the dictation systems. One example embodiment of the present disclosure transfers the numerical data, which may be DICOM Structure Report (SR) and/or HL7 inputs, from modalities into report templates on dictation systems, which reduces dictation process times by 20 percent to 40 percent.

FIG. 1 shows one example block diagram of a modalities-to-dictation transfer system 100. Transfer system 100 includes a network 103 that connects one or more modalities 105a, 105b, and 105c to a server 110 which is also connected to one or more dictation systems 115a and 115b. Clinical content, including patient and numerical data, produced by one or more modalities 105a, 105b, and 105c flows from at least one of the modalities 105a, 105b, and 105c via DICOM SR or HL7 messages over network 103 to server 110. Server 110 may have stored thereon a computer program or software application 120 capable of performing one or more functions to normalize the clinical content data and map the clinical content data to designated fields in a report generating application. The report fields may vary according to the vendor or manufacturer templates contained in each of dictation systems 115a and 115b in system 100. The clinical content may be sent to server 110 by a sending application associated with one or more modalities 105a, 105b and 105c.

One or more modalities 105a-105c and server 110 may be connected to network 103 through one or more network interfaces that allow each of modalities 105a-105c to send and receive content to and from another one of modality 105a-105c. In one example embodiment, content may be generated and maintained within an institution such as, for example, an integrated delivery network, hospital, physician's office or clinic, to provide patients and health care providers, insurers or payers access to records of a patient across a number of facilities. Sharing of content may be performed using network-connected enterprise-wide information systems, and other similar information exchanges or networks, as will be known in the art.

The network connecting the elements in system 100 may be any network, communications network, or network/communications network system such as, but not limited to, a peer-to-peer network, a hybrid peer-to-peer network, a Local Area Network (LAN), a Wide Area Network (WAN), a public network such as the Internet, a private network, a cellular network, a combination of different network types. Network 100 may be wireless, wired, and/or a wireless and wired combination network capable of allowing communication between two or more computing systems, as discussed herein, and/or available or known at the time of filing, and/or as developed after the time of filing.

Modalities 105a-105c may be any imaging content source. Imaging content sources may be imaging devices or equipment that generate imaging assets (e.g., medical images) that may be made available to one or more users of system 100 for transmitting or sending to another system such as, for example, dictation system 115. Modalities 105a-105c may refer to equipment that are used in a medical setting to generate images of at least a portion of a patient's body. In medical imaging, modalities 105a-105c are the various types of machines and equipment that are used to probe different parts of the body and acquire content showing data about the body. Examples of modalities include medical imaging equipment such as MRI, X-Ray, ultrasound machines, mammography machines and CT scanners.

In some alternative example embodiments, modalities 105a-105c may refer to any data content source that outputs data in HL7 format using a computing device, as will be known in the art. Examples of data content sources may be a desktop or laptop computer, a tablet computer, or a mobile device. One or more modalities 105a, 105b and 105c may include a sending application that sends the data captured by one or more modalities 105a, 105b and 105c to another communicatively connected device such as server 110.

One standard or specification for transmitting, storing, printing and handling information in medical imaging that may be used by modalities 105a-105c to communicate health-care related messages is defined by the Digital Imaging and Communications in Medicine (DICOM) organization. DICOM content may refer to medical images following the file format definition and network transmission protocol as defined by DICOM to facilitate the interoperability of one or more medical imaging equipment across a domain of health enterprises. DICOM content may include a range of biological imaging results and may include images generated through radiology and other radiological sciences, nuclear medicine, thermography, microscopy, microscopy and medical photography, among many others. DICOM content may be referred to hereinafter as images following the DICOM standard, and non-DICOM content may refer to other forms and types of medical or healthcare content not following the DICOM standard, as will be known in the art.

One other standard, which is also used to communicate healthcare-related or medical messages is the Health Level-7 (HL7) standard. The HL7 standard specifies guidelines for formatting content in order to allow hospitals and other healthcare provider organizations to interface with each other when the healthcare entities receive new content or when they wish to retrieve new content. While DICOM is typically used to encapsulate imaging-related content, HL7 may be used to standardize the format and context of other messages (i.e., non-DICOM content) that are exchanged between one or more information systems in a medical environment. Some of these messages may include data or content relating to the admission, discharge and/or transfer of patient, appointment scheduling, order entry, etc. Information that is generated using the HL7 standard may be referred to herein as an HL7 message.

Server 110 may be a computing device that is communicatively coupled or connected with one or more modalities 105a-105c via network 103 and receives content from modalities 105a-105c. The content, which may either be DICOM or HL7 messages, may be manipulated or processed in server 110 using application 120 to normalize the data from modalities 105a-105c. The data normalized using application 120 may then be sent to at least one of dictation systems 115a and 115b and PACS 120 for use in reporting and/or forms, as will be discussed in greater detail below.

Application 120 allows a user to create a user-configurable template which may be used to modify the data received from one or more modalities 105a, 105b and 105c. Modifying the data may include normalizing the data, converting the data from one format to another format and/or performing other transformation actions, in preparing the received data for use by another application or system such as, for example, dictation systems 115.

Dictation systems 115a and 115b may be clinical documentation software or solutions, such as voice recognition (VR) systems that typically receive data from modalities 105a, 105b and 105c through dictation by a user and transcribe the received data into a digital format suitable for inclusion in a report or study. In a typical medical environment, a radiologist generates reports for referring physicians by dictating the patient data captured by modality 105a, 105b and 105c to dictation system 115, and the dictation system transcribes the dictated data and generates reports which include the transcribed data.

Example dictation systems 115a and 115b may include systems that are able to receive DICOM content and/or HL7 messages. In the present disclosure, each of dictation systems 115a and 115b may be connected to modalities 105a, 105b and 105c via server 110 that hosts application 120. As will be discussed in greater detail below, modalities 105a, 105b and 105c generate patient clinical data, send the data to server 110, and server 110 sends the data to dictation system 115. The data sent from server 110 to dictation system 115 may be normalized or formatted by application 120 and mapped to a report template of dictation system 115 so that the normalized data received by dictation system 115 may be auto-populated into the report template. Such auto-population eliminates need for the dictation of clinical data typically done by the physician when drafting the clinical report. The report templates of dictation systems 115a and 115b may vary by dictation system manufacturer or vendor.

Figure 2:
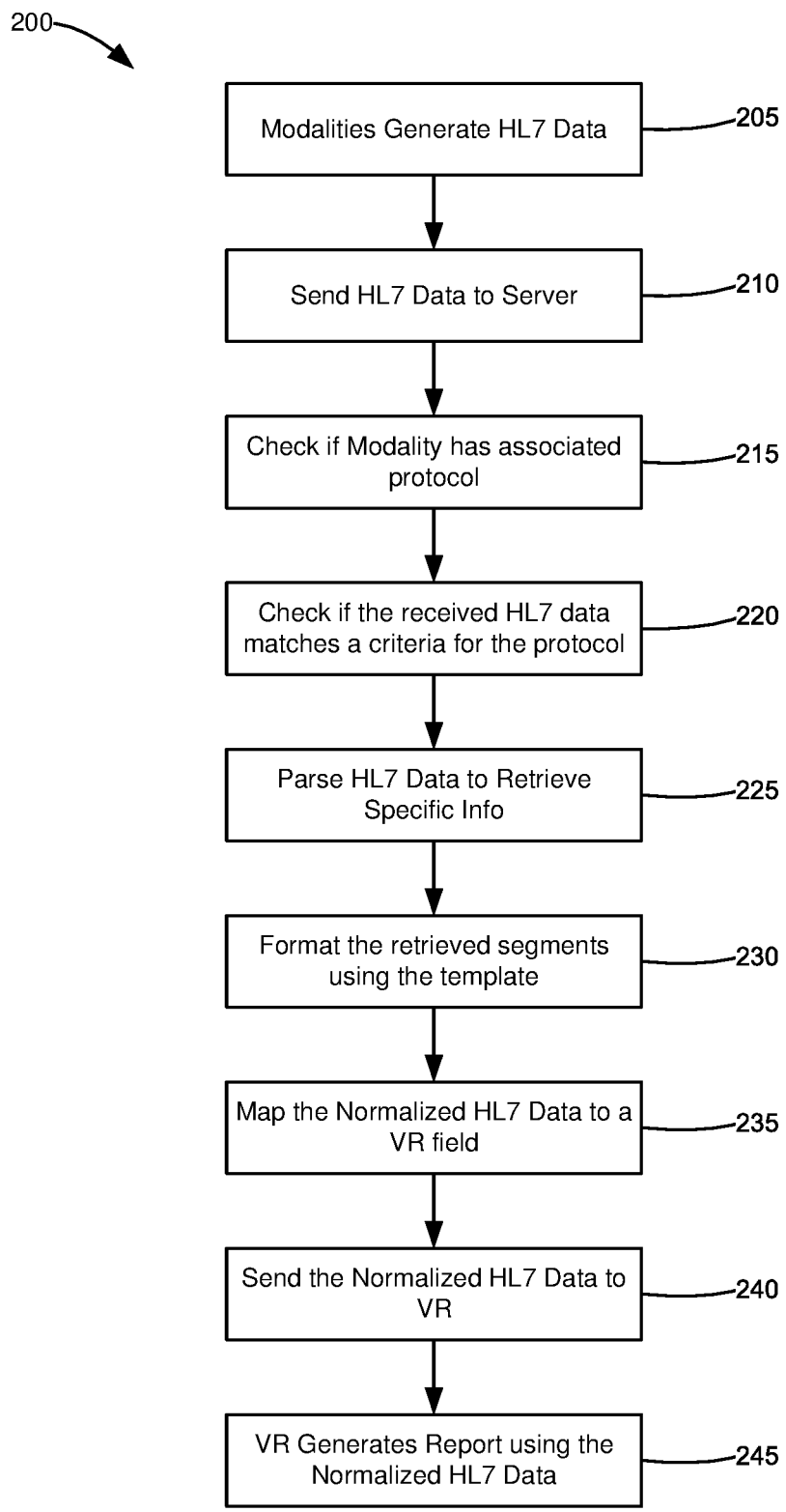
FIG. 2 shows one example method of transferring clinical data generated by one or more modalities to at least one dictation system.

FIG. 2 shows one example method 200 of transferring clinical data generated by one or more modalities 105a-105c to at least one dictation system 115. The data to be transferred will be manipulated before the transferring to ensure that the data is in a format that is consistent with dictation system 115 that receives the data. Dictation system 115, upon receiving the data, may be able to easily generate a report using the data by auto-populating one or more fields in a report template with the corresponding normalized data.

Method 200 may be performed in server 110 using application 120. In some alternative example embodiments, method 200 may be performed by any computing device that receives the data generated by one or more modalities 105a-105c and has one or more instructions to normalize the data to prepare it for transfer and use by one of dictation systems 115a and 115b.

At block 205, at least one of the modalities 105a-105c in system 100 generates clinical data. For example, a radiologist may perform a medical procedure, such as an ultrasound scan on a patient, using an ultrasound machine (one of modalities 105a-105c) in example system 100. For illustrative purposes, modalities 105a-105c that generate data for use in example method 200 are direct imaging machines (e.g., ultrasound machine). In other example embodiments, other types of computing devices, software applications, data archives or databases that contain data generated from modality equipment may be used as the data source or data generator in block 205.

At block 210, the data generated by modalities 105a-105c is sent to server 110 for transferring to at least one of dictation systems 115. Example modalities 105a-105c that generated the data may be associated with server 110 such that server 110 is able to receive the data from the originating source or machine (e.g., one of modalities 105a-105c). Associating modality 105a-105c with server 110 may include registering modality 105a-105c as a device in server 110 that is authorized to send data to server 110.

In one example embodiment where multiple modalities 105a-105c send data to server 110, ports may be used to organize incoming messages from the various source modalities 105a-105c into groups called "matching groups". The matching groups may then be configured to include one or more formatting templates such that incoming messages from modalities 105 that belong to the matching group will be normalized using the formatting templates associated with the matching group. Ports enable application 120 to group messages in at least two ways: by originating source (e.g., DICOM or HL7 modalities), and by a matching criterion such as a user-selected data field included in a message sent from the originating source to server 110. In one example embodiment, a user may indicate or specify a port to receive messages from all HL7 modality sources connected with server 110. The port may then group the messages by a criterion such as, for example, HL7 message types, which is located in MSH 9 of the HL7 message.

The formatting templates may be modified or otherwise controlled by a user. Modifications may include, but are not limited to, disabling the formatting template such that the formatting template may not be used to format the received data; enabling the formatting template; or changing some formatting rules in the formatting template. The option to enable or disable the formatting template denotes whether or not application 120 will process the data received from one or more modalities 105a-105c using the formatting template. If a formatting template is disabled, data that matches the protocol associated with the formatting template will not be processed by application 120. When the formatting template is disabled, the matching data will also not be sent to the corresponding dictation system 115. In other example embodiments, if there is no formatting template assigned to a protocol that matches the data, application 120 may not process data received from modality 115.

Figure 3:
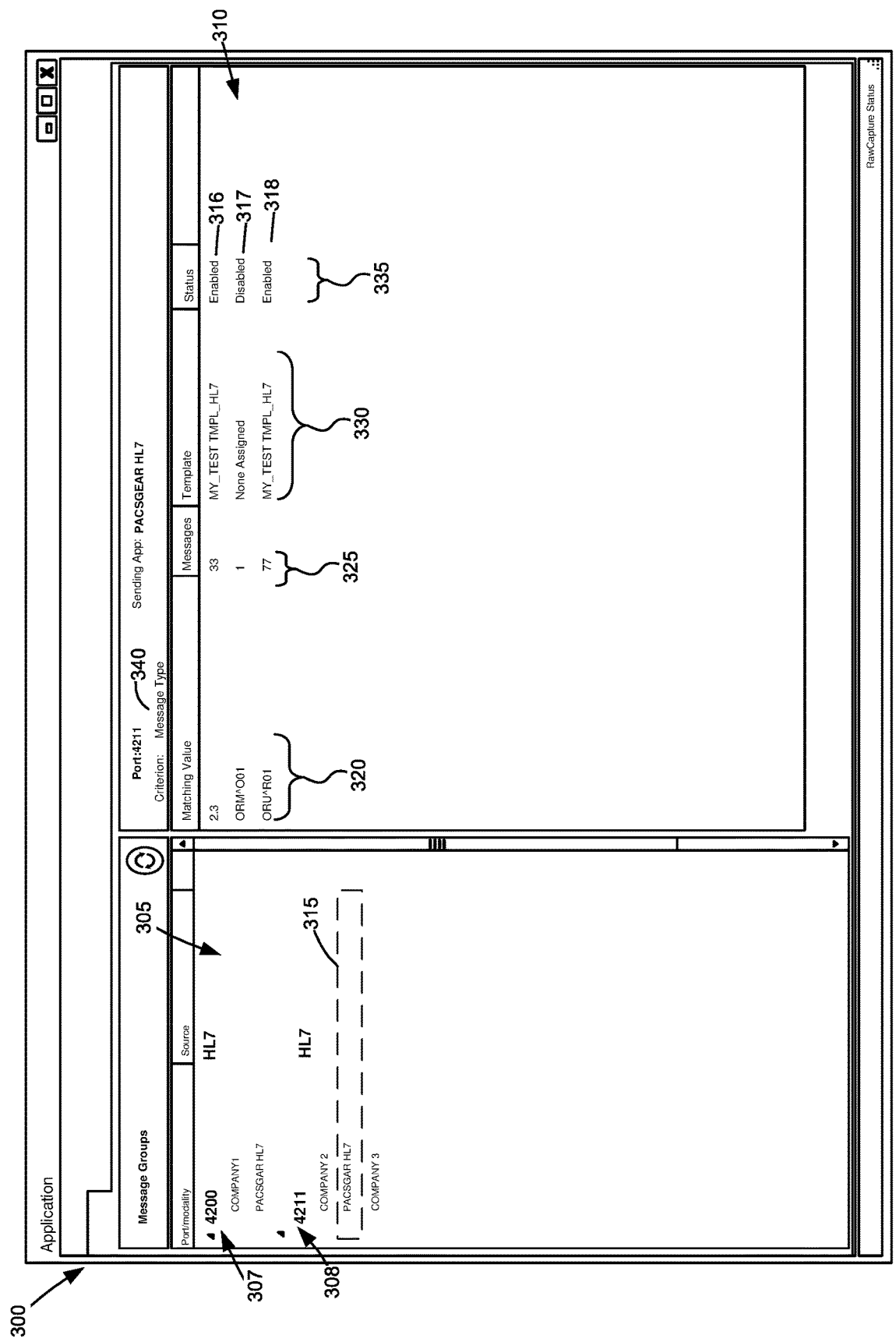
FIG. 3 shows one example main display screen or user interface (UI) of an application, which may be used in normalizing HL7 data received from the one or more modalities.

FIG. 3 shows one example main display screen or user interface (UI) 300 of application 120, which may be used in normalizing data received from one or more modalities 105a-105c. UI 300 may be a main screen such as a home page for application 120 that includes a modality panel 305 for showing or displaying a list of sources of incoming messages which may be modalities 105a-105c. Each of the items listed in modality panel 305 represents a sending application of modality 105a-105c that generates data to be sent to and received by server 110. In this example embodiment, the sending applications are grouped into ports 307, 308, designated as Port 4200 and Port 4211, respectively. The grouping of the example modalities listed in modality panel 305 may be set by the user. In UI 300, selecting a sending application, such as example "PACSGEAR HL7" 315, from modality panel 305 displays, in a message type panel 310, protocols that have been created for and are associated with the selected sending application 315.

Message type panel 310 shows rows of example message types 316-318 having protocols that are associated with sending application 315 selected on panel 305. Each row of message types 316-318 contains data from sending application 315 that match a criterion that is specified when the user configures each of example ports 307, 308. Each row of message types 316-318 contains information corresponding to a Matching Value column 320, a Messages column 325, a Template column 330, and a Status column 335.

Matching Value column 320 contains the names of the messages types that match the criterion (e.g., "Message Type") set in a Criterion field 340 that have been set (in this example for Port 4211 and sending application "PACSGEAR HL7"), and Messages column 325 shows the number of messages received from sending application 315. Template column 330 in message type panel 310 shows the template that is assigned to message types 316-318 (in this example, "MY_TEST TMPL_HL7", None assigned and "MY_TEST TMPL_HL7", respectively), and Status column 335 shows if message types 316-318 is enabled or disabled.

Application 120 may only forward messages to dictation systems 115 that belong to enabled message types 316-318. The user may enable or disable the protocols created, and the status of each of the protocols may be shown in Status column 335. Enabling one or more reporting protocols will initiate a manipulation of messages received by server 110 from a selected sending application 315 if the messages received from selected sending application 315 successfully meets a criteria set for each of the protocols. For example, as shown in FIG. 3, if sending application "PACSGEAR HL7" 315 is selected, messages or clinical data received from modality PACSGEAR HL7 through Port 4211 that meet the criteria for set for the 2.3 and ORU^R01 will be manipulated or formatted for the 2.3 and ORU^R01 protocols using the MY_TEST TMPL_HL7 template since each of those protocols are enabled.

Referring back to FIG. 2, at block 220, application 120 determines or checks if the received message from the sending application contains a value that matches a criterion for a matching protocol. In example UI 300, application 120 checks Criterion field 340 for the protocol (i.e., the Message Type) associated with example sending application 315 and determines, using the criterion, if the incoming message matches a specified message type (e.g. "ORU^R01").

For illustrative purposes, selected sending application 315 generates HL7 content and sends the HL7 content to server 110 for processing using application 120. In the example illustrated in FIG. 3, application 120 checks if the clinical data received from sending application 315 (i.e., "PACSGEAR HL7") has a Message Type that matches any one of the values listed in the Matching Value column 320: "2.3", "ORM^O01" or "ORU^R01." Other HL7 message types may also be used such as, for example, ADT for admit discharge transfer messages, DFT (detailed financial transaction), RAS (pharmacy or treatment administration), among others as will be known in the art.

In the example shown in FIG. 3, example port 4211 includes a criterion to check the Message Type of all incoming messages from modalities 105 that were grouped under port 4211 to determine if they match any of the values indicated in Matching Value 320 column. For illustrative purposes, protocol panel 310 shows the receipt of thirty-three incoming messages for matching group 316 in Messages column 325 from one or more modalities 105a-105c having study descriptions that match the value "2.3."

If the received HL7 content matches any of the criteria for the protocol, and if the protocol is enabled, one or more data manipulation techniques such as those indicated in the template associated with the matching protocol will be performed. In another example embodiment, application 120 only checks for matching values for protocols that are listed as enabled for the selected modality. For example, the seventy-seven messages received from one or more modalities 105a-105c having a Message Type that matches the value "ORM^R01" will be normalized using the "MY_TMPL_HL7" formatting template since matching group 318 for corresponding matching value 320 is enabled, as shown in Status Column 335.

Referring back to FIG. 2, when the protocol is enabled for a matching group, the messages received from modalities 105a-105c that match the criterion may be parsed to identify specific portions of the messages that are deemed relevant for the formatting using the formatting template associated with the protocol (block 225). The parsing is performed to enable the formatting template associated with the protocol to retrieve the data to be formatted from the content generated or sent by source modality from one of modalities 105a-105c.

Application 120 may use different kinds of formatting templates such as, for example, DICOM and HL7 formatting templates, to normalize and map the values of each type of message. Each type of formatting template may contain data from different dictation systems 115a and 115b and modalities 105a-105c, and the user may configure them in different ways. When a formatting template is assigned to a message type, the user configures how application 120 maps the specific values from specific sending applications to designated fields in the report template provided by dictation system 115.

Figure 4:
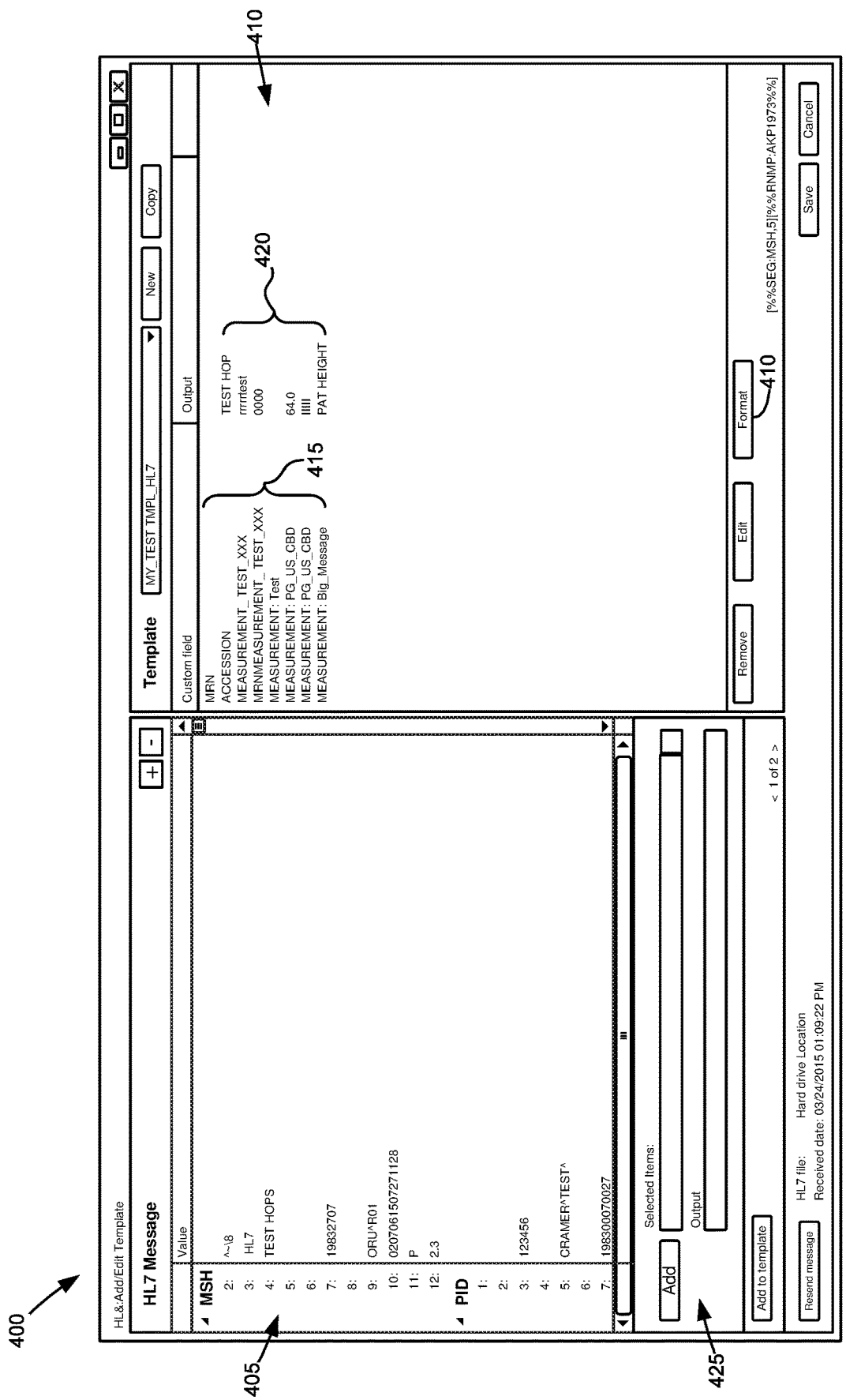
FIG. 4 shows one example user interface for a user-configurable HL7 formatting template for use in formatting or normalizing one or more HL7 messages received from one or more source modalities.

FIG. 4 shows one example user interface for a user-configurable HL7 formatting template 400 for use in formatting or normalizing one or more HL7 messages received from one or more source modalities 105a-105c. Formatting template 400 may be created by a user once and stored for future or multiple uses. All data or messages received from the associated modality 105a-105c that matches the value set in the criterion for the protocol will be formatted using formatting template 400. It will be understood that template 400 may be edited. For example, a user may wish to add a formatting rule or to delete an existing formatting rule from formatting template 400. Formatting template 400 may also be deleted or disabled by the user at any given time.

HL7 formatting template 400 may be associated with a protocol for one or more modalities 105a-105c such that when HL7 clinical messages or data is received from the one or more modalities 105a-105c, application 120 determines if the received clinical data contains information that matches a criterion for formatting template 400. Upon a positive determination, formatting template 400 may be used to extract clinical data from the received HL7 message and format or normalize the extracted HL7 clinical data using one or more formatting options. The specific data from the received HL7 message that was extracted using formatting template 400 may be mapped to designated report fields 415 associated with dictation system 115 using identifier-data value or key-value pairs.

In example HL7 formatting template 400, HL7 Message template panel 405 shows the clinical data or content received from sending application 315 while panel 410 shows the clinical data from the HL7 message mapped to designated report fields 415 associated with a report template from dictation system 115. HL7 formatting template 400 also shows a function that allows a user to add an item from the HL7 message to HL7 formatting template 400, as shown in Add panel 425.

Creation of the HL7 formatting template 400 may be performed by a user at least once prior to receiving HL7 messages from one or more modalities 105a-105c. After the HL7 formatting template has been created, all data received from the associated modality will be checked for matching protocols and formatted using the rules set in HL7 formatting template 400, as will be discussed in greater detail below. Formatting template 400 may be edited, deleted, enabled, and disabled by the user at any given time after the formatting template has been created.

When HL7 formatting template 400 is associated with the protocol, the data parsed from the HL7 content may be normalized and/or formatted using the rules set in formatting template 400 (at block 230). Normalization of the data from one or more modalities 105a-105c allows a consistent presentation of data such as numeric data across various devices. Using a number of normalization techniques, a user may format all incoming measurements or information that meet one or more criteria as set in the protocol to be presented in a consistent and more intuitive format for referring physicians.

Example HL7 formatting template 400 shows Output column 420 containing formatted values corresponding to clinical data extracted from the incoming HL7 message that has been mapped to designated report fields 415 associated with dictation system 115. The formatted values will be sent to destination dictation system 115 in the format shown in Output column 420 for auto-populating the report template when a report is generated. Designated report fields 415 may be identifiers of one or more fields in the report template of dictation system 115 where the data at Output 420 will be auto-populated into. The identifiers of the designated report fields may be associated with a location in the report template where the Output 420 data will be entered during auto-population of the report template with the data from the HL7 message.

In an alternative example embodiment where no formatting option was selected in formatting template 400, values received from modality 115 will be mapped to the designated fields associated with dictation system in their original format and then sent to dictation system 115 for report generation.

The format of the value may be configured by the user once and will then be applied to all the values that correspond to a certain field in formatting template 400, and mapped to corresponding report fields 415 in a report template of dictation system 115. This will be performed for all HL7 messages that meet the criterion for the protocol associated with formatting template 400.

Figure 5A:
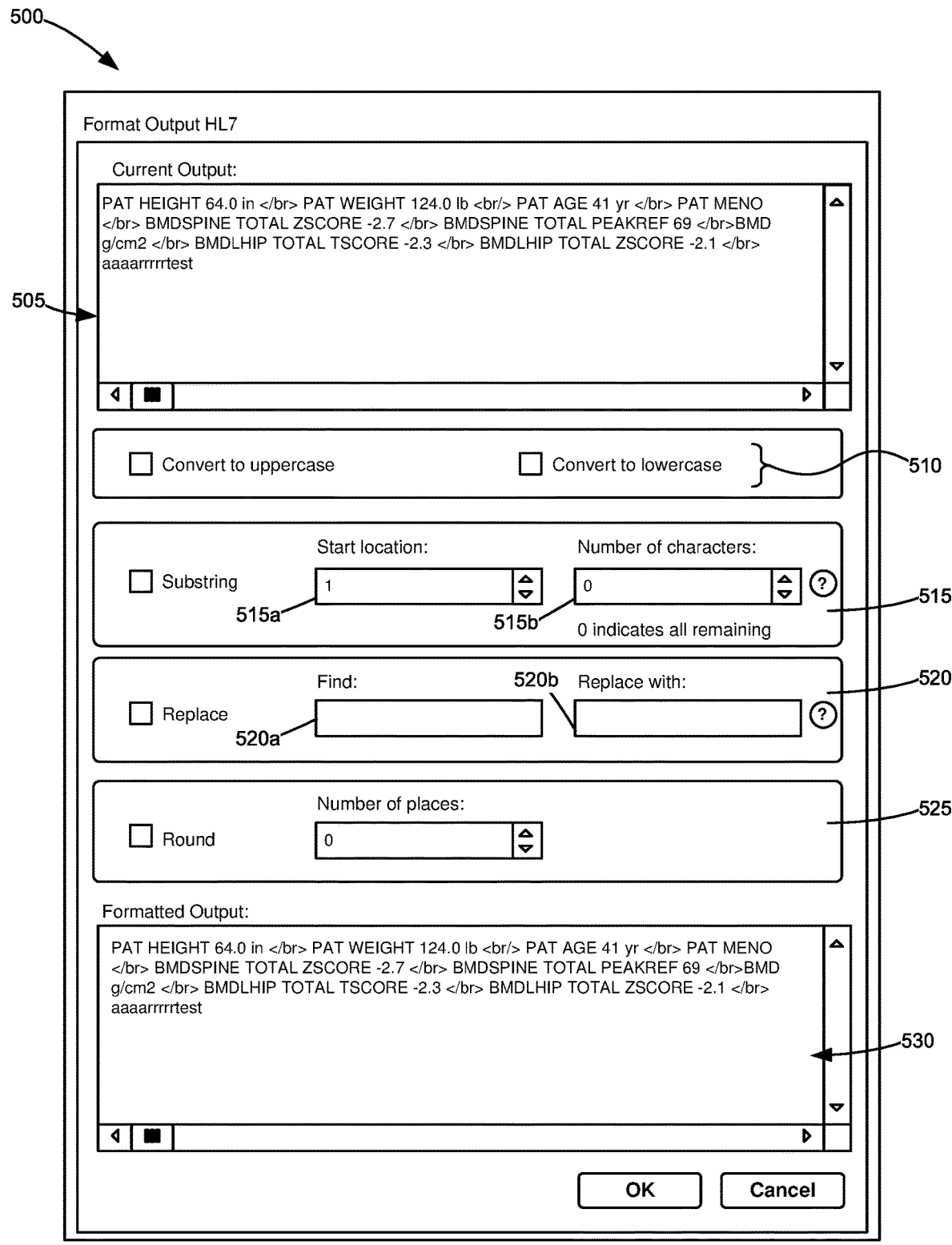
FIGS. 5A-5E show example formatting dialog user interfaces including formatting options for use in normalizing HL7 messages.

FIG. 5a shows an example formatting dialog user interface 500 including formatting options for use in normalizing HL7 messages. Formatting dialog 500 may be viewed by highlighting or selecting one of designated fields 415 and clicking on a format button 430 (shown in FIG. 4). The Current Output section 505 shows a portion of an HL7 message in a format as it was received from the source modality from one of modalities 105a-105c. Using example formatting dialog 500, formatting options may be selected in order to normalize the specified portion of the HL7 message for a consistent output for use in generating reports in dictation systems 115.

The normalization options available may include case conversion options 510, substring extraction option 515, replace option 520, and a round-off option 525.

Figure 5B:
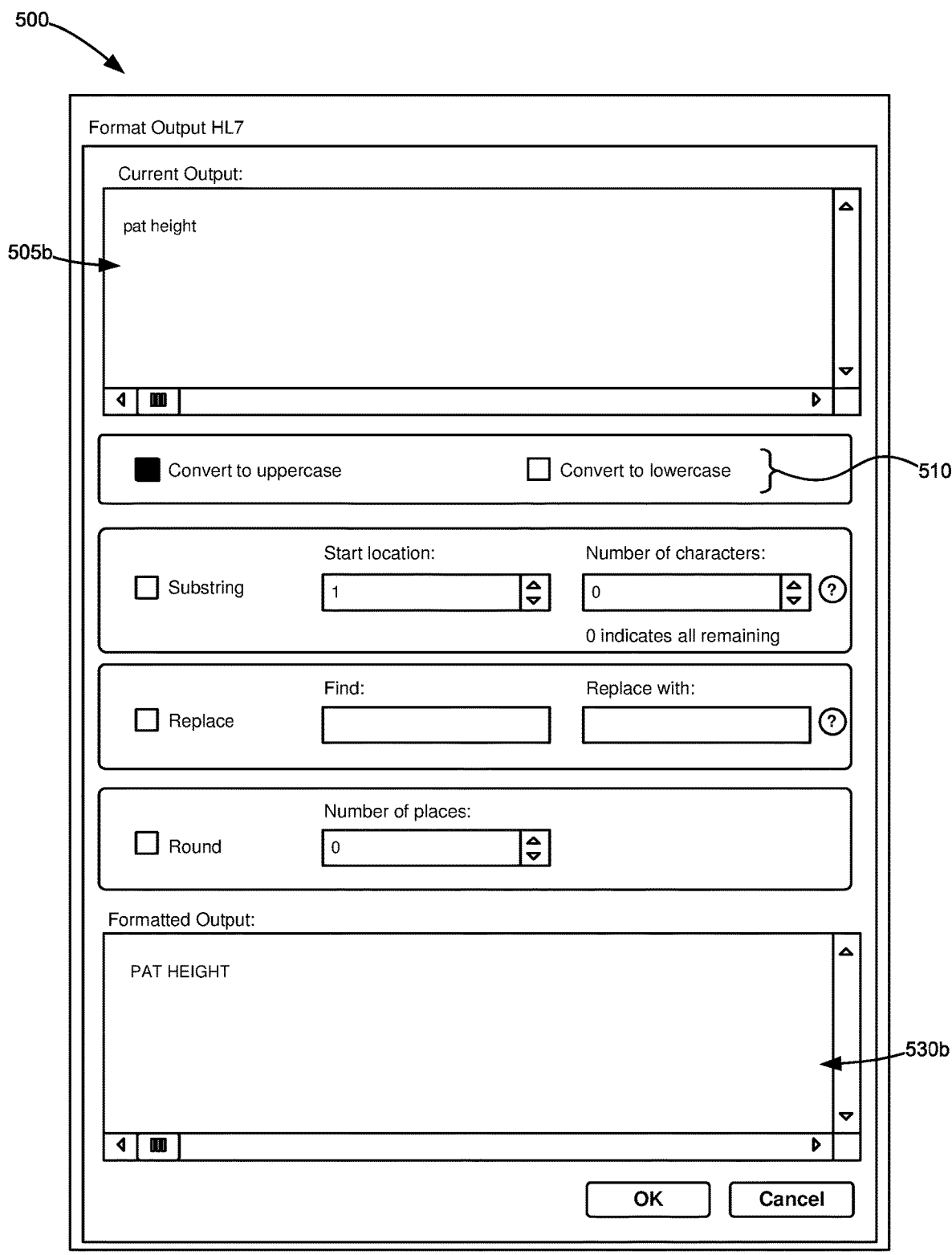

FIG. 5b shows an example formatting dialog 400 where Current Output section 505b shows a value from HL7 message "pat height" that is set to be normalized using Case Conversion options 510. Case conversion options 510 are available for selection by a user when the user chooses to convert the selected portion of the clinical data to one of uppercase and lowercase. In the example shown in FIG. 5b, the user chooses to convert the Current Output data at Current Output 505b into uppercase, thereby formatting the data from "pat height" to "PAT HEIGHT" as shown in Formatted Output 530b. When the user presses OK, the formatted output "PAT HEIGHT" will be mapped to the designated report field 415 (shown in FIG. 4) and will be sent to dictation system 115 for auto-populating a report template when generating reports.

Figure 5C:
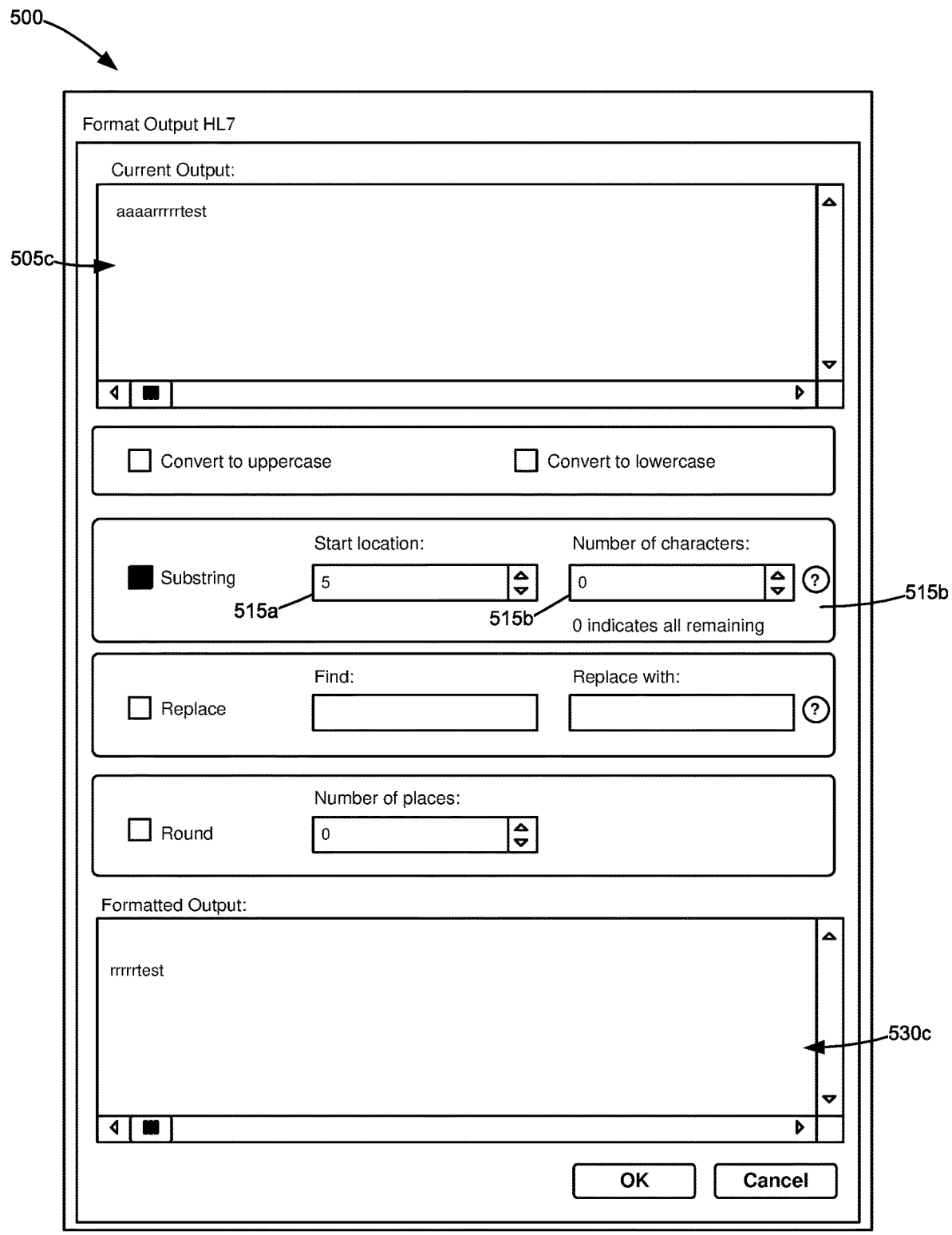

FIG. 5c shows an example formatting dialog 400 where Current Output section 505c shows a value from an incoming HL7 message "aaaarrrrrtest" that is set to be normalized using substring extraction option 515. Substring extraction option 515 is available for a user to specify or opt to output at least a portion of the string, or a sub-value of the chosen value in the Current Output section 505c. In the substring extraction option 515, a start location 515a where the extraction of the sub-value of the chosen value starts may be indicated by the user. A number of characters 515b that indicates the remaining characters for the sub value may also be indicated. For example, the start location for the substring is set at 5 with the number of characters remaining set at 0 which indicates that all remaining characters after the fifth character will be extracted using the substring extraction option 515. These set of options will then extract from the current output 505c the formatted output value 530c "rrrrrt-est" which will then be mapped to the designated report field and sent to dictation system 115 for use in generating reports.

Figure 5D:
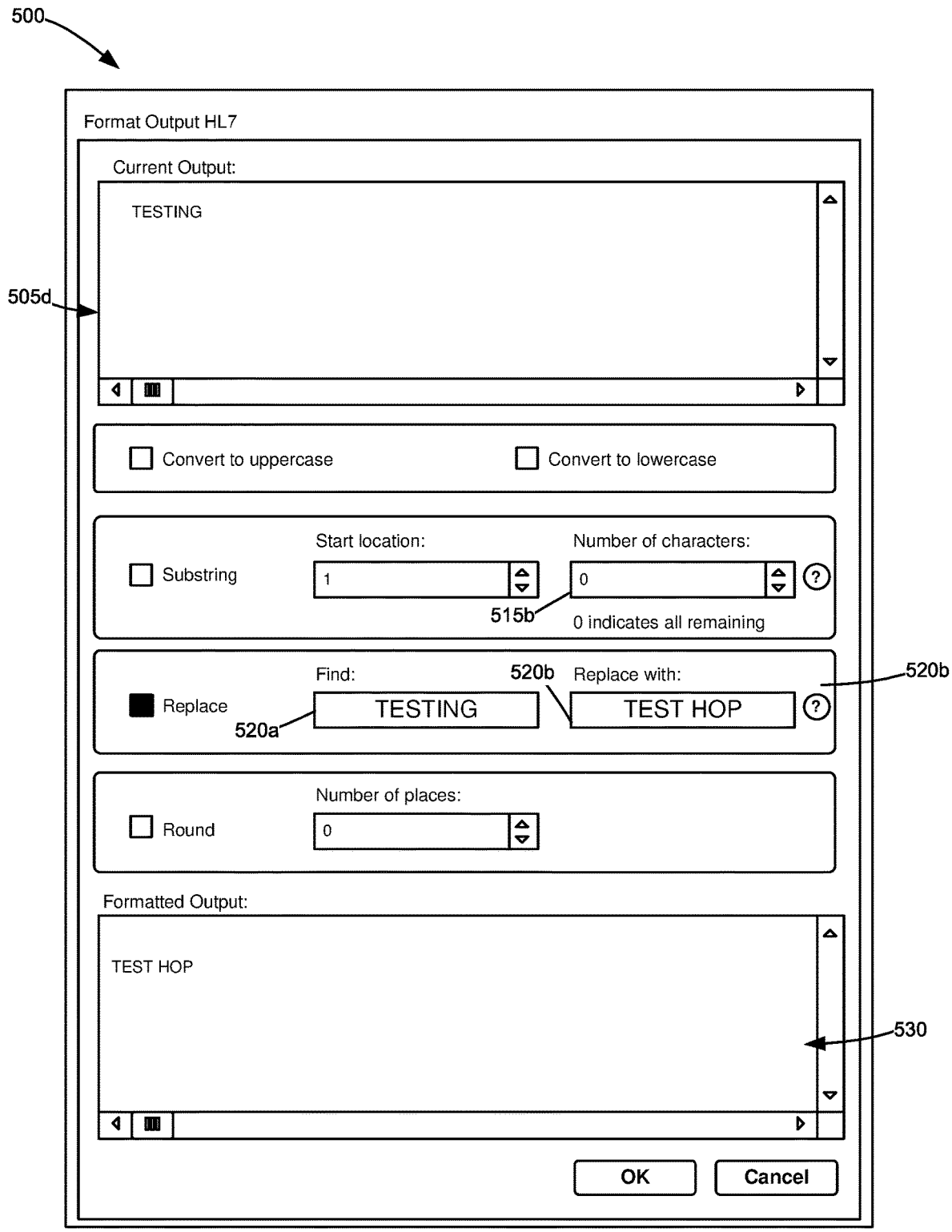

FIG. 5d shows Replace option 520 available as a normalization option which replaces the specified characters in Current Output section 505d with another value. For example, the current value to be replaced (e.g. "TESTING") may be specified at an input field 520a, with the new characters (e.g. "TEST HOP") to replace the current value indicated at an input field 520b. The formatted output of the value "TESTING" will now be "TEST HOP" which will be mapped to the designated report field and sent to dictation system 115 for use in generating reports.

Figure 5E:
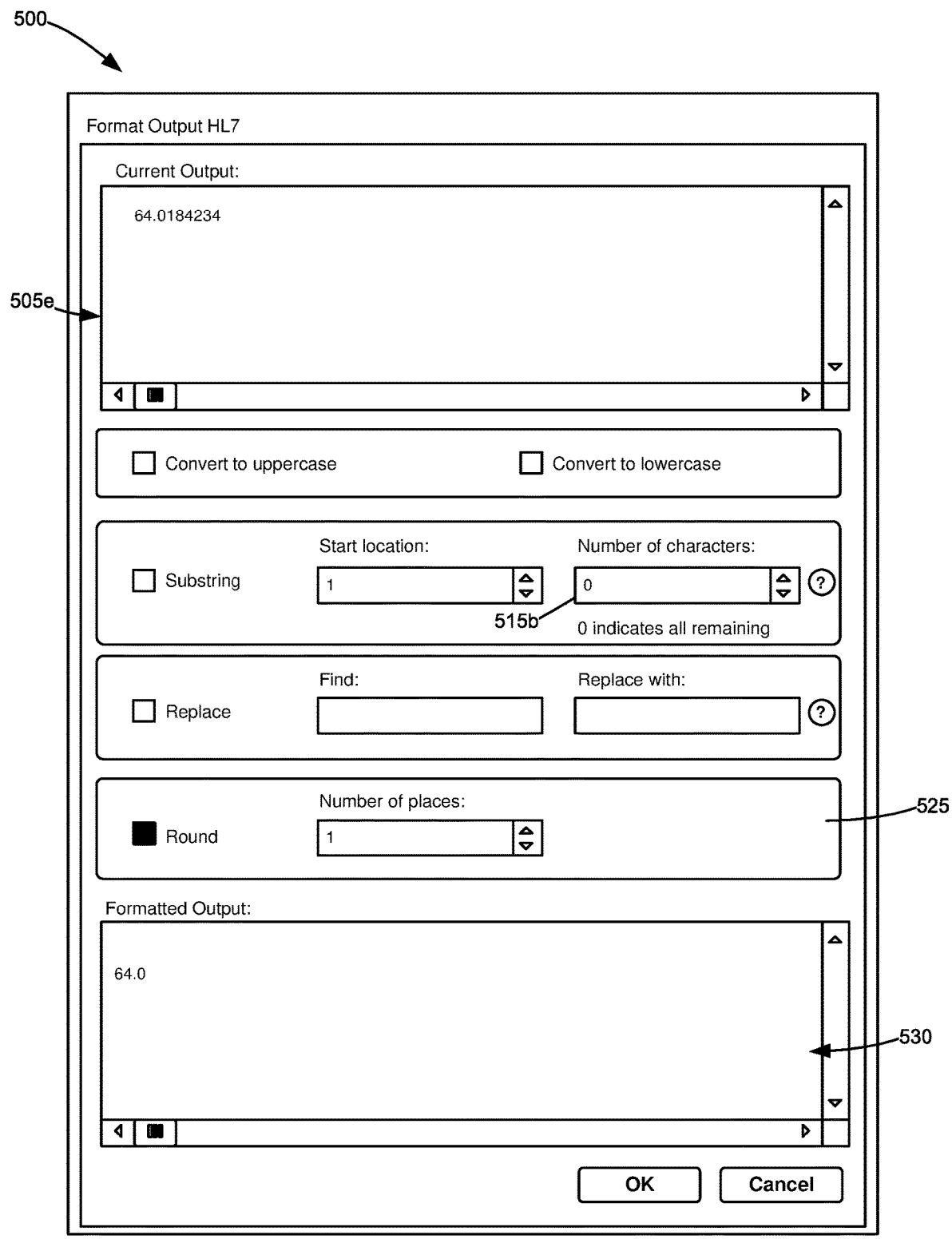

FIG. 5e shows Rounding option 525 which shows an example formatting dialog 400 that checks the value of Current Output section 505 and determines if it is a number then rounds it off to a specified number of places. For example, if application 120 determines that the value of Current Output section 505 is a number, the Rounding option 525 is made available. When the user selects this normalization option and specifies the number of places to "1", application 120 rounds off the current output at 505e "64.0184234" to one decimal place to generate the formatted output "64.0." The formatted output of the value "64.0184234" will now be "64.0" which will be mapped to the designated report field and sent to dictation system 115 for use in generating reports.

A preview of the formatted value may be provided using a Formatted Output panel 530. In the example shown in formatting dialog 500, no formatting option has been selected for use in normalizing the values in Current Output 505. Thus, the values in the Current Output 705 will be mapped to the corresponding dictation system field (at block 235) and sent to the dictation system for report generation (at block 240). Similarly, if at least one of the formatting options was selected in formatting template 500, the formatting option will be applied to the current or selected value, and the formatted output will be mapped to the corresponding dictation system field and sent to the dictation system for report generation.

A selected dictation system report template that is used to generate reports receives the values from application 120 in server 110 and inserts the values in the corresponding portions of the report, as indicated in the formatting template 400, to generate a report having the formatted values (at block 245). If a value corresponding to a designated field in the dictation system report template is missing or incorrect, application 120 may prevent the transmission of the formatted values to dictation system 115 or prevent the user from signing off of application 115 or otherwise prevent processing of the received clinical data until such value is manually entered or corrected. In other example embodiments, if a value corresponding to a designated field in the dictation system report template is missing, dictation system 115 may prevent the transmission of the formatted values to dictation system 115 or prevent the user from signing off of dictation system until the value is manually entered. Such conditions prevent the generation of incomplete reports or reports with missing values and mitigate possible errors in parsing. Proper configuration of the mapping function minimizes the need for manual intervention.

In one example embodiment, HL7 data may be configured and sent as an HL7 ORU message for dictation systems that may require an HL7 Order Results Unit (ORU) format. Application 120 may include one or more functions for packaging data that is received from the source modality in a first format into a second format that may be required by the destination systems (i.e. dictation systems).

As discussed above in one example embodiment of the present disclosure, HL7 messages are received by application 120 from the one or more modalities 105. HL7 messages may have single-segment or multi-segment fields. A single-segment field is a field in a segment that appears once in an HL7 message while a multi-segment field appears more than once in an HL7 message.

Typically, multi-segment fields in an HL7 message are OBX segments, where each repeated segment contains different information. HL7 OBX may be observation segments in an HL7 message that are primarily used to contain key clinical results or observations which may typically include reporting information within a reporting message. OBX segments may carry clinical information that may be needed by receiving personnel, such as a physician, to interpret the observation being made, rather than actual information about the test results. An OBX segment may transmit a single observation fragment and may be used more than once in the message, such as is the case for multi-segment fields.

FIG. 6 shows an example HL7 message 600 with multi-segment fields such as, for example, OBX segments 605. In the example message 600, OBX segments 605 are separated by a carriage return. Each OBX segment 605, which are represented as one OBX segment 605 per line in the example HL7 message may start with a three-character string that identifies the type of segment. Each segment of the HL7 message may also contain one specific category of information. For example, the three-character string of "MSH" 610 may be used as the first segment for HL7 messages, which includes a field that identifies the message type, e.g. "MSH". It will be known in the art that the message type indicated in an HL7 message may determine the expected segment types in the message. Each of OBX segments 605 may contain fields that are separated by a vertical or pipe I and sub-fields that are separated by a caret ˆ. For example, field 615 is separated from other fields using the pipe, and example sub-field 620 is separated and indicated to be a sub-field using a caret.

Figure 7:
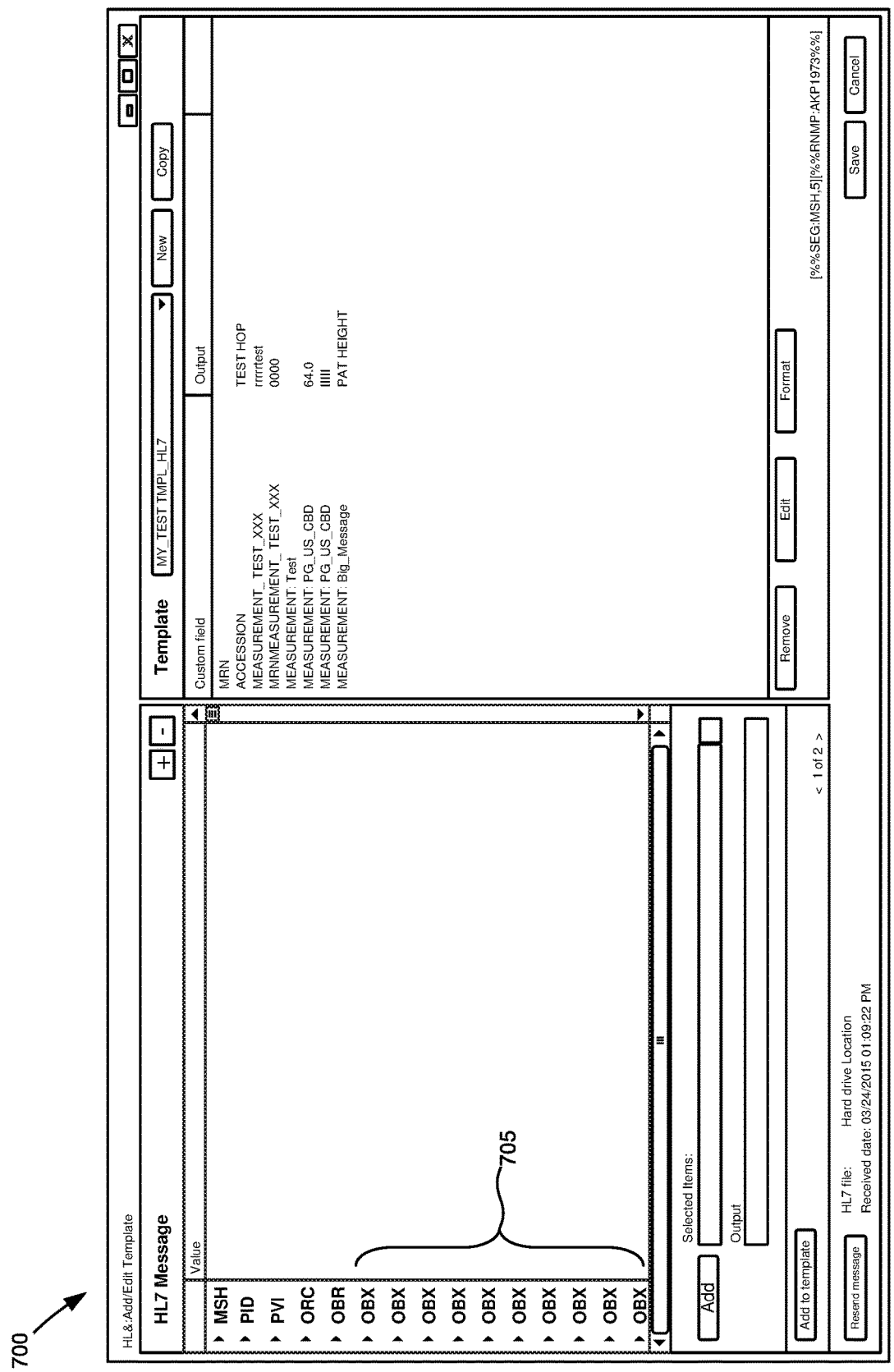
FIG. 7 shows a user interface of application showing an HL7 message with multiple OBX multi-field segments.

When a user wishes to add a value from one of the repeating segments in an HL7 message, application 120 provides options that allow the end user to parse the information from the repeating segments and extract specific information from the repeated segments. FIG. 7 shows a user interface 700 of application 120 showing an HL7 message with multiple OBX multi-field segments 705.

When the user wishes to select a field within a particular multi-field (OBX) segment from one of the OBX segments 705, the user may select or expand one of OBX segments 705 and click an Add button provided in the user interface 700 to add a field from the chosen segment.

Figure 8:
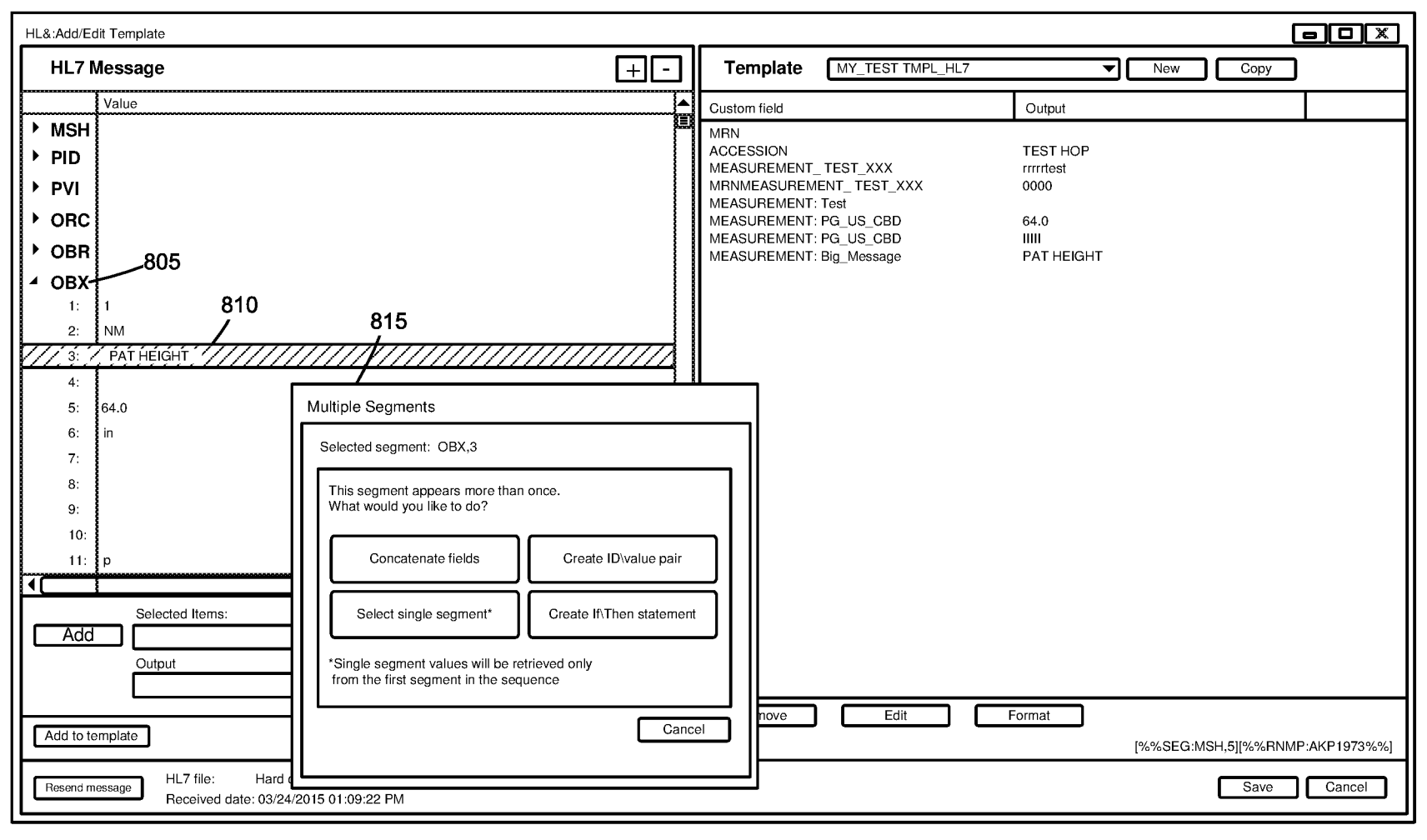

FIG. 8 shows user interface 700 displaying an example OBX segment 805 with a field 810 selected by the user. When the user chooses to add selected field 810, application 120 automatically detects that the selected field belongs to a repeating segment and a dialog 815 may then be displayed showing options for adding the field from the selected repeated segment.

In one example embodiment of adding a field from a repeating segment, a user may select a single segment where values may be retrieved from a specified segment in the sequence. This option may be selected from dialog 815 using the Select Single Segment 820 option. When the user selects this option, application 120 may display another user interface (not shown) for the user to choose a sub-field within the chosen field and the user may then add this choice to the formatting template. In one example embodiment, when the user has selected the sub-field from the chosen field, the value may be retrieved from the first repeating segment that application 120 encounters within a HL7 message. For example, if PAT HEIGHT is selected as the field in an OBX segment from which to retrieve data, the PAT HEIGHT field will be selected on the first OBX segment among the repeating segments that is included in the example HL7 message. If this option has been added to the formatting template, the PAT HEIGHT field will be selected on the first OBX segment among the repeating segments that is included in all incoming HL7 messages that meet the criterion of the protocol associated with the formatting template. In this example, the values in the PAT HEIGHT field will be retrieved from each of the first OBX segment that is included in the example HL7 message. As shown in dialog box 815, single segment values may be retrieved only from the first segment in the sequence.

In another example embodiment of adding a field from a repeating segment, concatenation of the fields may be selected by the user wherein application 120 will be configured to select a user-chosen field from the repeating segment and concatenate the values to be retrieved from the chosen fields together from each of the repeating segments. This option is provided in dialog 815 as the Concatenate fields 825 option.

Figures 9A, 9B:
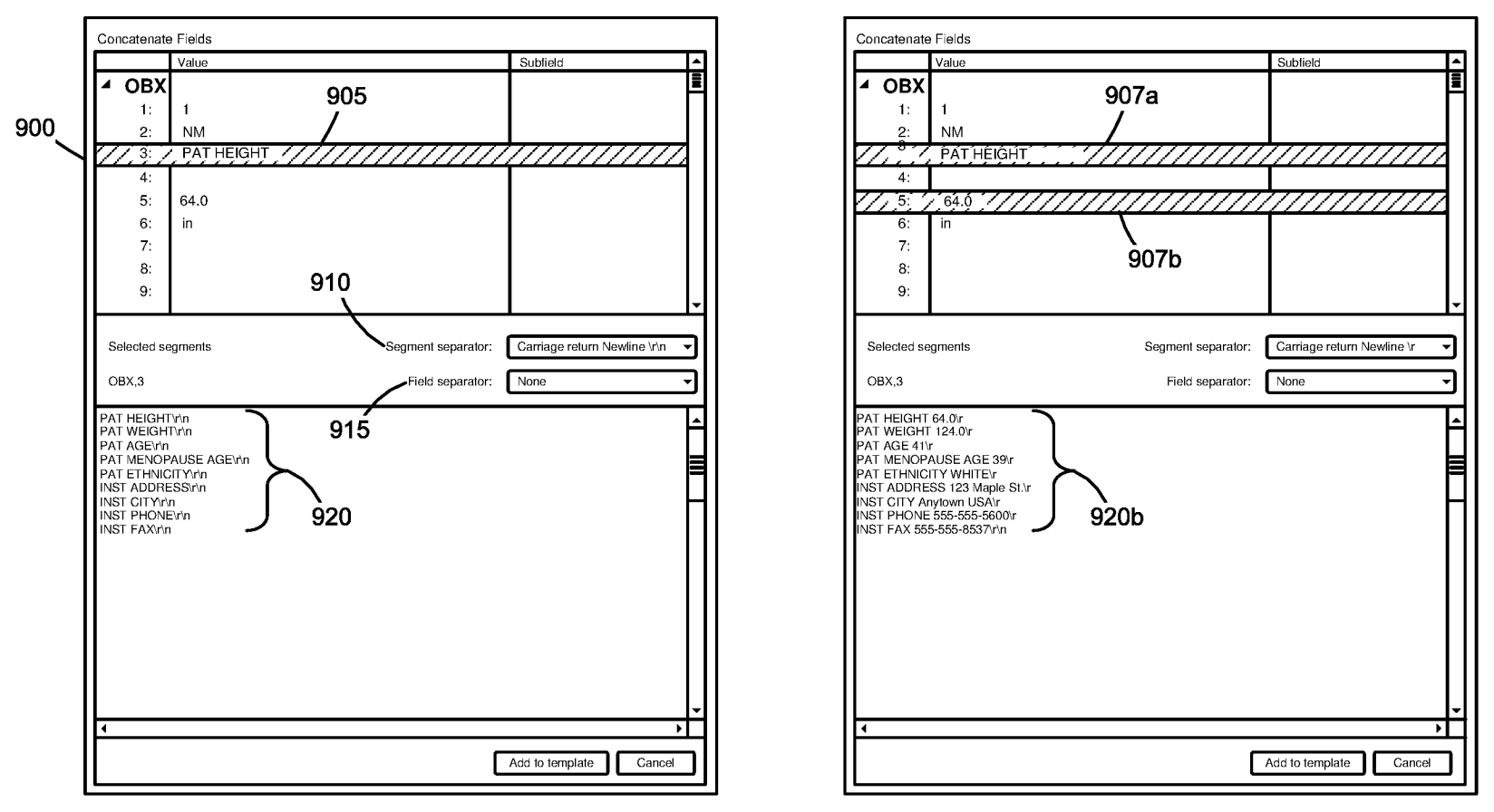

FIG. 9A shows an example user interface 900 for selecting a field from which values will be extracted from repeating segments and concatenated together. Using example user interface 900, a user may select field "3" 905 as the field from which value will be extracted from the repeating segments of the HL7 message. If an example HL7 message has ten repeating OBX segments, application 120 may extract all values in field "3" from each of the ten repeating OBX segments and concatenate each of the values into one field.

A segment separator 910 may be selected that separates the values extracted from one segment to another, and a field separator 915 that separates values from one field to another. Example segment and/or field separators may include a carriage return, a new line, tilde, space, comma, caret and HTML breaks among others. User interface 900 may also include a formatted output 920 that shows the extracted and concatenated values from the specified field of repeating segments in the HL7 message.

FIG. 9B shows an example user interface 900 where a user may select multiple fields 907a and 907b (e.g. fields "3" and "5") from which values will be extracted from the repeating segments and concatenated together. When multiple fields are selected, the values from each of the fields will be extracted from each of the repeating segments of an HL7 messages and concatenated together using the indicated segment separator 910 and/or field separator 915, as shown in formatted output 920b.

When the user has selected the field from which values are to be extracted and has configured the segment and/or field separators to be used, the settings may be added to a formatting template. Once added to a formatting template, HL7 messages that meet the criterion of the protocol associated with the formatting template may be normalized using the settings such that the values from the selected field from the repeating segments of the incoming HL7 messages are extracted and concatenated based on the configured settings. The extracted and concatenated values are then mapped to a field in a report template of dictation system 115 for use in report generation.

Figure 10:
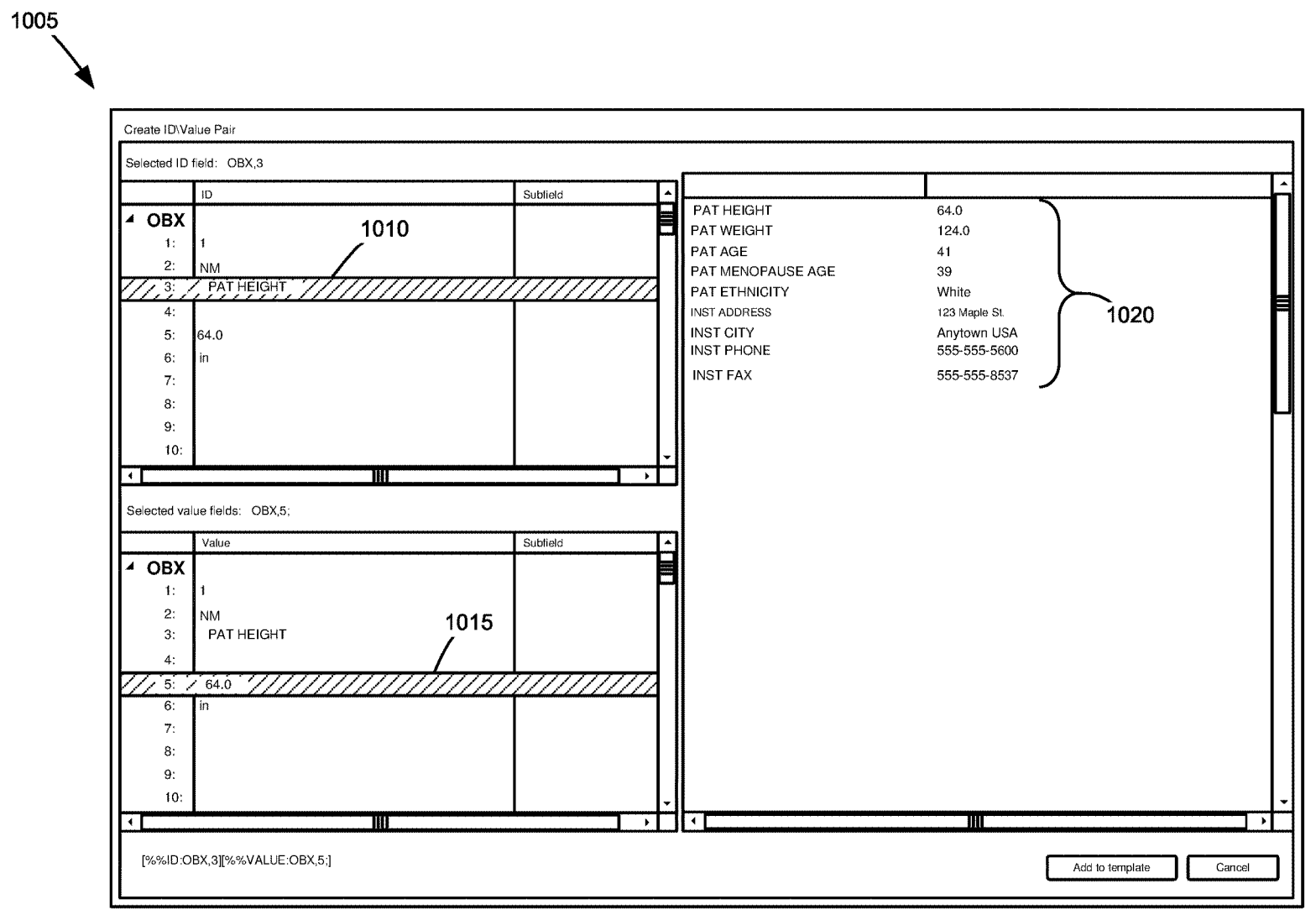

In another example embodiment of extracting values from repeating segments of an HL7 message, a user may create an ID/value pair from the repeating segments. This option may be provided in Create ID/value pair option in dialog 815. FIG. 10 shows an example user interface 1005 of application 120 for creating an ID/value pair from the repeating segment. Using the user interface 1005, the user may select a first field 1010 (e.g. field "3") from a repeating segment to be set as the ID, and a second field 1015 (e.g. field "5") to be set as the value. Example formatted output using this selection option is displayed at Message Output 1020. Once this ID/value pair has been set and added to a formatting template, application 120 will extract the values from the selected fields and set then as an ID/value pair to be mapped to a field in the report template and sent to dictation system 120 for use in report generation. Application 120 processes HL7 messages associated with the formatting template with an ID/value pair applied to it and use selected field 1010 as the ID sent to dictation system 120, and the selected value field 1015 as the value associated with that ID. For example, PAT HEIGHT/64.0 will be sent as one of the ID/value pairs of the HL7 message to dictation system 120. All other values found in the HL7 from OBX,3 and OBX,5 fields are paired and sent to dictation system 120 as seen in Message Output 1020.

Another example embodiment of extracting values from repeating segments in an HL7 messages including setting an if/then statement. This option may be made available to the user through Create If/Then Statement option 835 from dialog 815. There is no definite number of repeating segments included in a typical HL7 message and determining where a particular data can be found in any one of the repeating segments may be difficult. Creating an if/then statement allows a user to locate a specific piece of information within the repeating segment by defining a value to locate within the segment, regardless of where the value is located in which field in the segment.

Figure 11:
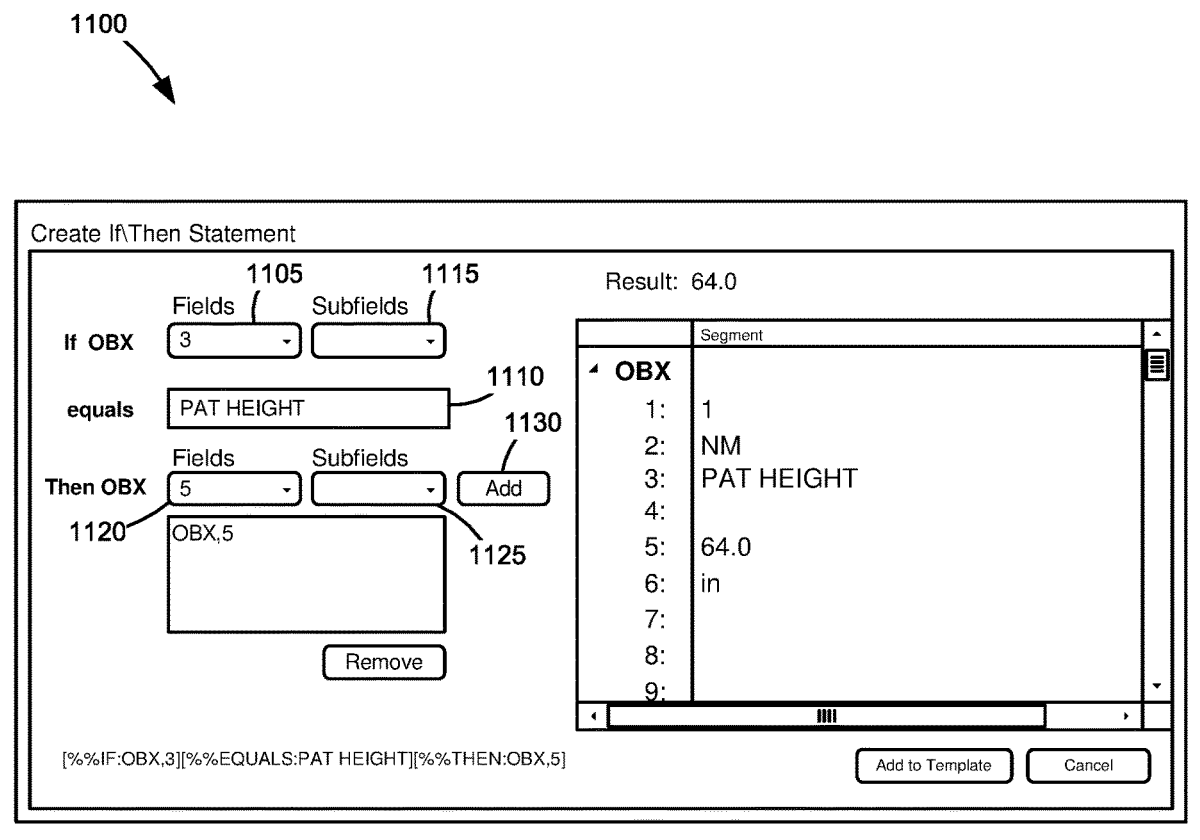

FIG. 11 shows an example user interface 1100 showing configurable options for use in setting an if/then statement. The options are used to specify the value to be extracted from one or more repeating segments in an example HL7 message 1105. In the example user interface 1100 shown, a user has requested that when a repeating segment of type OBX is encountered, application 120 checks field "3" as set in input field 1110, and check to see if the value of that field matches the phrase "PAT HEIGHT" as specified in input field 1115. A subfield input field 1120 may also be provided to allow the user to further make specific the "if" statement.

If application 120 determines that the "if" statement matches the set value "PAT HEIGHT", then the fifth segment from the segment being checked may then be used as the value for this selection. The fifth segment or field "5" of the example HL7 message 1105 is specified at input field 1125 at the "then" portion of the if/then statement. The result of the if/then statement may be seen at 1130 being "64.0". The user may use subfields as the field to match or as a field for the value. The user may also add multiple fields for any of the values. The extracted value may then be mapped to a field in a report template of dictation system 115 for use in report generation.

It will be understood that the example applications described herein are illustrative and should not be considered limiting. It will be appreciated that the actions described and shown in the example flowcharts may be carried out or performed in any suitable order. It will also be appreciated that not all of the actions described in FIG. 2 need to be performed in accordance with the example embodiments of the disclosure and/or additional actions may be performed in accordance with other example embodiments of the disclosure.

Many modifications and other example embodiments of the disclosure set forth herein will come to mind to one skilled in the art to which these disclosure pertain having the benefit of the teachings presented in the foregoing descriptions and the associated drawings. Therefore, it is to be understood that the disclosure is not to be limited to the specific embodiments disclosed and that modifications and other embodiments are intended to be included within the scope of the appended claims. Although specific terms are employed herein, they are used in a generic and descriptive sense only and not for purposes of limitation.

What is claimed is:

1. A method of retrieving one or more values from a Health Level 7 (HL7) clinical data from one or more sending applications on a server or modality for transferring to a dictation system, comprising:

receiving HL7 clinical data having one or more multi-segment fields from at least one modality that generates the HL7 clinical data;

parsing the HL7 clinical data received from the at least one modality that generates the HL7 clinical data;

accessing a formatting template for use in normalizing the parsed HL7 clinical data, the formatting template including one or more format settings, a selection of one or more fields from a specified multi-segment field of the HL7 clinical data from which one or more values are to be retrieved, and a retrieval setting that specifies a type of the one or more multi-segment fields from which to retrieve the one or more values;

retrieving the one or more values of the selection from the one or more multi-segment fields having the type from which to retrieve the one or more values as specified in the retrieval setting, wherein the retrieving the one or more values of the selection of the one or more fields from the specified multi-segment field of the parsed HL7 clinical data includes retrieving the one or more values of a field of a first applicable segment from the one or more multi-segment fields of the HL7 clinical data;

normalizing the retrieved one or more values by formatting the retrieved one or more values using the one or more format settings set in the formatting template; and sending the one or more normalized values to the dictation system for use in generating a report by the dictation system.

2. The method of claim 1, wherein the normalizing the retrieved one or more values includes concatenating the retrieved one or more values and formatting the concatenated one or more values based on the one or more format settings included in the formatting template.

3. The method of claim 2, further comprising mapping the one or more normalized values to at least one field in a report template in the dictation system by associating the one or more normalized values to the at least one field in the report template for use in generating a report by the dictation system.

4. The method of claim 3, wherein the dictation system generates the report by replacing the at least one field in the report template of the dictation system with the concatenated one or more normalized values based on the mapping of the one or more normalized values to the at least one field in the report template.

5. The method of claim 1, wherein the retrieval setting in the formatting template indicates a field identifier from which to retrieve the one or more values from each of the one or more multi-segment fields.

6. The method of claim 1, wherein the retrieval setting in the formatting template includes an if/then statement wherein if a field from the multi-segment field meets a criterion set in the if/then statement, the one or more values from the field that meets the criterion are retrieved.

7. The method of claim 1, wherein the retrieval setting in the formatting template includes a first field having a value to be retrieved and specified as an ID and a second field having a value to be retrieved and paired with the ID.

8. The method of claim 1, wherein the formatting the one or more values includes rounding off the retrieved values to a number of decimal places as set in the formatting template for the at least one field that the values are mapped to.

9. A method of normalizing one or more portions of an Health Level 7 (HL7) message from one or more modalities that generate the HL7 data for use by a dictation system in generating a report, comprising:

receiving the HL7 message from at least one modality of the one or more modalities that generate the HL7 data, the HL7 message having one or more multi-segment fields;

parsing the HL7 message received from the at least one modality;

retrieving a formatting template for use in normalizing the parsed HL7 message, the formatting template including one or more format settings and a selection of one or more fields from a specified multi-segment field of the HL7 message from which one or more values are to be retrieved;

retrieving the one or more values of the selection of the one or more fields from the specified multi-segment field of the parsed HL7 message as indicated in the formatting template, wherein the retrieving the one or more values of the selection of the one or more fields from the specified multi-segment field of the parsed HL7 message includes retrieving the one or more values of a field of a first applicable segment from the one or more multi-segment fields of the HL7 message;

normalizing the retrieved one or more values from the specified multi-segment field by formatting the retrieved one or more values based on the one or more format settings included in the formatting template; and transmitting the one or more normalized values to the dictation system for use in a report by the dictation system.

10. The method of claim 9, wherein the retrieving the one or more values of the one or more fields is performed by determining if a multi-segment field from the one or more multi-segment fields of the HL7 message contains a specific text and upon positive determination, retrieving the one or more values of the one or more fields of the one or more multi-segment fields that contains the specific text.

11. The method of claim 10, wherein the determining if the multi-segment field from the one or more multi-segment fields of the HL7 message contains the specific text is set by a user in the formatting template as an if/else statement wherein if the multi-segment field contains the specific text that is set by the user, the retrieving of the one or more values from the one or more multi-segment fields is performed.

12. The method of claim 9, wherein the formatting the one or more values includes replacing the values with another value as set in the formatting template.

13. The method of claim 9, wherein the formatting the one or more values includes extracting a portion of the value to generate a substring for sending to the dictation system.

14. The method of claim 9, further comprising determining if the HL7 message received is to be processed using the formatting template by determining if a metadata value of the HL7 message matches a criterion associated with the formatting template.

15. The method of claim 14, further comprising upon determining if the metadata value of the HL7 message matches the criterion associated with the formatting template, performing the parsing of the HL7 message.

16. A system for populating one or more reports using data from one or more Health-Level 7 (HL7) messages, comprising:

at least one modality that generates HL7 data, the at least one modality including a sending application, wherein the modality that generates HL7 data is medical imaging equipment;

a computing device including a non-transitory computer readable storage medium having instructions to:

receive a HL7 message from the sending application of the at least one modality that generates HL7 data, the HL7 message having one or more multi-segment fields;

parse the HL7 message received from the at least one modality that generates HL7 data;

retrieve a formatting template for use in normalizing the parsed HL7 message, the formatting template indicating a selection of one or more fields to be retrieved from a specified multi-segment field of the HL7 message from which one or more values are to be retrieved;

retrieve the one or more values of the selection from of the one or more fields of from the specified multi-segment field as indicated in the formatting template, wherein retrieving the one or more values of the selection of the one or more fields from the specified multi-segment field of the parsed HL7 message includes retrieving the one or more values of a field of a first applicable segment from the one or more multi-segment fields of the HL7 message;

normalize the retrieved one or more values of the one or more fields from the specified multi-segment field by formatting the retrieved one or more values based on one or more format settings included in the formatting template; and a dictation system communicatively connected to the computing device and receives the one or more normalized values and generates the report using the one or more normalized values, wherein the computing device includes one or more instructions to map the one or more normalized values to at least one field in a report template in the dictation system by associating the one or more normalized values to the at least one field in the report template.

17. The system of claim 16, wherein the dictation system generates the report using the one or more normalized values by automatically populating at least one field in the report template with the one or more normalized values.

18. The system of claim 16, wherein the dictation system generates the report using the one or more normalized values by automatically populating at least one field in the report template with the one or more normalized values.

19. The system of claim 16, wherein the one or more fields to be retrieved from the specified multi-segment field of the HL7 message is indicated in the formatting template as one or more retrieval rules.

* * * * *

UNITED STATES PATENT AND TRADEMARK OFFICE
CERTIFICATE OF CORRECTION

Page 1 of 1

PATENT NO. : 10,769,363 B2
APPLICATION NO. : 15/160851
DATED : September 8, 2020
INVENTOR(S) : Christopher Eugene Leitner It is certified that error appears in the above-identified patent and that said Letters Patent is hereby corrected as shown below:

In the Claims

At Column 19, Lines 9-10, "to be retrieved" should be removed.

At Column 19, Line 13, "from" should be removed.

At Column 19, Line 14, "of" should be removed.

Signed and Sealed this
First Day of June, 2021

Drew Hirshfeld
*Performing the Functions and Duties of the*
*Under Secretary of Commerce for Intellectual Property and*
*Director of the United States Patent and Trademark Office*